(12) United States Patent
Hamoy et al.

(10) Patent No.: US 12,186,225 B2
(45) Date of Patent: Jan. 7, 2025

(54) AMBULATING ABDUCTOR PHYSICAL REHABILITATION WEDGE

(71) Applicants: Dustin P. Hamoy, Baltimore, MD (US); Jeffrey Steven Cunningham, Nottingham, MD (US)

(72) Inventors: Dustin P. Hamoy, Baltimore, MD (US); Jeffrey Steven Cunningham, Nottingham, MD (US)

( * ) Notice: Subject to any disclaimer, the term of this patent is extended or adjusted under 35 U.S.C. 154(b) by 297 days.

(21) Appl. No.: 17/959,023

(22) Filed: Oct. 3, 2022

(65) Prior Publication Data
US 2023/0135047 A1 May 4, 2023

Related U.S. Application Data

(60) Provisional application No. 63/275,342, filed on Nov. 3, 2021.

(51) Int. Cl.
*A61F 5/01* (2006.01)
(52) U.S. Cl.
CPC .................. *A61F 5/0193* (2013.01)
(58) Field of Classification Search
CPC .......... A61F 5/01; A61F 5/0193; A63B 69/00; A63B 69/0057–0062; A63B 69/36; A63B 69/3676; A41D 13/05; A41D 13/0525; A41D 13/0537; A61G 7/065; A61G 7/075; A61G 7/0755
See application file for complete search history.

(56) References Cited

U.S. PATENT DOCUMENTS

| | | | | |
|---|---|---|---|---|
| 4,392,489 A * | 7/1983 | Wagner, Sr. | .......... | A61F 5/0193 D24/190 |
| 5,681,270 A * | 10/1997 | Klearman | ................ | A61F 5/012 128/845 |
| 5,895,366 A * | 4/1999 | Bzoch | .................. | A61F 5/0193 128/DIG. 20 |
| 6,179,756 B1 * | 1/2001 | Bertolucci | ......... | A63B 23/0488 482/131 |
| 6,859,939 B1 * | 3/2005 | Osburn, Sr. | .......... | A41D 13/018 128/869 |

FOREIGN PATENT DOCUMENTS

FR 1165669 A * 10/1958

* cited by examiner

*Primary Examiner* — Michelle J Lee
(74) *Attorney, Agent, or Firm* — Nadya Reingand

(57) ABSTRACT

A wearable physical rehabilitation device configured to separate the thighs of a subject to promote proper posture of the pelvis while walking is provided. The device comprises a supporting belt fitted around the subject's waist, a 3D wedge-like PU-foam structure arranged between the subject's thighs, a saddle-shaped structure for receiving the subject's buttocks, and a hollow control handle arranged anteriorly relative to the subject's body. The 3D wedge-like structure has a hole and is attached to the belt by a pair of ascending straps each passing through the hole. Each of a pair of lateral straps passes through the hole and attaches the 3D wedge-like structure to and around one of the thighs. The handle has one pair of descending straps extending therefrom and attaching to the saddle-shaped structure and another pair of ascending straps extending therefrom and attached to each other behind the subject's neck.

10 Claims, 5 Drawing Sheets

AMBULATING ABDUCTOR PHYSICAL REHABILITATION WEDGE

FIELD OF THE INVENTION

The present disclosure relates generally to the field of physical rehabilitation during ambulation. More particularly, the present disclosure relates to a wearable physical rehabilitation device that is configured to separate the inner thighs of a subject for the purpose of promoting proper posture of the pelvis while walking.

BACKGROUND OF INVENTION

Thus far in the rehabilitation industry, there is no device that can decrease the so-called Q angle (which is an angle from the outer hip to the inner ankle on the same leg of a subject) directly from a source (i.e., the hip) in a functional manner and simultaneously affect positively the low back, knees, hips, and ankles of the subject. In the rehabilitation industry, there are only devices for increasing hip abduction in a static position, which however do not allow for dynamic movements while having increased abduction, such as walking. Thoracolumbar braces are also known, but for the purpose of up righting posture from the spine up rather than from the pelvis up. Other rehabilitation balance training techniques are also known, such as aquatic therapy pools, which have been shown to improve balance through buoyancy, but they do not allow a human body to be properly postured for standalone balance control. Furthermore, suspended treadmill walking has also been shown to improve balance and posture using body suspension overhead, coupled with treadmill motion to mimic normal walking mechanics; however, the suspended treadmill walking does not allow the human body to be lifted from the posterior pelvic saddle through anterior applied forces by a rehabilitation specialist during ambulation.

U.S. Pat. No. 8,214,952 B2 (10 Jul. 2012) discloses a stationary non-dynamical abductor pillow that is used for supine patients (laying on their back) after surgery to keep the hip in alignment for healing purposes. This stationary non-dynamical apparatus attaches from the hips to the ankle and is only worn while stationary in the bed. Moreover, rehabilitation specialists are often challenged with patients displaying improper forward head/neck posture, resulting in a forward bending at the waist (hips). In conjunction with the forward bending, these same patients also generally tend to have what is called "knock knees" or "flat feet". All these ailments are affected by the alignment of the hip joints on the pelvis.

SUMMARY OF THE INVENTION

This summary is provided to introduce a selection of concepts in a simplified form that are further described below in the detailed description. This summary is not intended to identify key features of the present disclosure, nor is it intended to be used to limit the scope of the present disclosure.

It is an objective of the present disclosure to provide a physical rehabilitation device that, when worn by a subject, allows separating the inner thighs of the subject for the purpose of promoting proper posture of the pelvis while walking.

The objective above is achieved by the features of the independent claim in the appended claims. Further embodiments and examples are apparent from the dependent claims, the detailed description, and the accompanying drawings.

According to an aspect of the present disclosure, a wearable physical rehabilitation device is provided. The device comprises a supporting or fastening belt configured to be fitted around a waist of a subject, a 3D wedge-like structure made of polyurethane (PU) foam (e.g., Blue high-density PU foam) and configured to be arranged between thighs of the subject, a saddle-shaped structure configured to receive buttocks of the subject, and a control handle arranged anteriorly relative to the body of the subject. The 3D wedge-like structure has a tubular through hole and is attached to the belt by a pair of ascending adjustable-length straps each passing through the hole. The device further comprises a pair of lateral adjustable-length straps each passing through the hole and attaching the 3D wedge-like structure to and around one the thighs of the subject. The device further comprises a pair of descending adjustable-length straps each extending from the control handle and configured to attach the control handle to the saddle-shaped structure, as well as an additional pair of ascending adjustable-length straps extending from the control handle and configured to attach to each other behind a neck of the subject. By using this device, it is possible to provide a proper functional Q angle. Furthermore, this device can significantly improve a standing posture, decrease an overall fall risk by widening the lower extremities base of support, decrease a "pes planus" foot posture (or flat feet) by externally rotating the femur and transferring forces onto the lateral border of a foot, as well as decrease medial knee stress by also transferring these forces to the lateral surface of the knee joint. It should also be noted that the straps lacing through the control handle more freely eliminates one-sided force production by allowing it to slide freely as needed for the subject's stability and avoid twisting or torquing of the subject's body during use of the physical rehabilitation device. Further advantages of the device thus configured are the following:

respiratory: it can improve breathing as it will promote upright standing, therefore better chest expansion;

vascular: it can improve a blood flow as it will promote venous and arterial pumping from a more aligned upright position to reduce the force needed from the heart to distribute blood to the extremities of the human body; and digestion: it can improve the moving of food thru the digestive track and waste through the bowls, thereby decreasing the amount of forward flexion at the waist, which can restrict the movement of food for absorption of nutrients.

In one embodiment, the 3D wedge-like structure further comprises two lateral recesses, each shaped to fit an inner surface of one of the thighs of the subject. With these recesses, the 3D wedge-like structure becomes more stationary in place, as well as may be worn more comfortably while walking.

In one embodiment, the 3D wedge-like structure is configured as a 3D isosceles trapezoidal wedge. The wedge of such shape is more comfortable to wear while walking.

In one embodiment, the 3D wedge-like structure further comprises a variable density pliable filler shaped to be inserted into the tubular through hole. By using such a filler, it is possible to provide proper inter-thigh spacing, support, rigidity, integrity and structural stability, according to the subject's physical needs.

In one embodiment, each strap in at least one of the pair of ascending adjustable-length straps, the pair of lateral adjustable-length straps, the pair of descending adjustable-length straps and the additional pair of ascending adjustable-length straps is made of nylon fabric. Nylon fabric is exceptionally strong, as well as pliable and resilient, for which reason it may be easily positioned to provide a proper fixation of the 3D wedge-like structure between the thighs of the subject. By using the nylon-fabric straps, it is possible to ascend them up just right above the iliac crests bilaterally.

In one embodiment, each strap in at least one of the pair of ascending adjustable-length straps, the pair of lateral adjustable-length straps and the pair of descending adjustable-length straps has two strap portions attached to each other by using a Velcro or buckle attachment means. These types of the straps are convenient to use and can provide a proper fixation of the 3D wedge-like structure between the thighs of the subject.

In one embodiment, each strap of the pair of ascending adjustable-length straps has ends attached to the supporting belt anteriorly and posteriorly by using a Velcro attachment means. This type of the straps is convenient to use and can provide a proper fixation of the 3D wedge-like structure between the thighs of the subject.

In one embodiment, each strap of the pair of descending adjustable-length straps has an end attached to each side of the saddle-shaped structure by using a Velcro attachment means. The Velcro attachment means may allow the straps to be attached to and detached from the saddle-shaped structure more easily and efficiently.

In one embodiment, the straps of the additional pair of ascending adjustable-length straps are configured to attach to each other behind the neck of the subject by using a Velcro attachment means. The Velcro attachment means may allow the straps to be attached to and detached from each other more easily and efficiently.

Other features and advantages of the present disclosure will be apparent upon reading the following detailed description and reviewing the accompanying drawings.

BRIEF DESCRIPTION OF THE DRAWINGS

The present disclosure is explained below with reference to the accompanying drawings in which:

FIG. 3A shows a front isometric view of the 3D wedge-like structure, and FIG. 3B shows a top view of the 3D wedge-like structure;

DETAILED DESCRIPTION OF THE INVENTION

Figure 1:
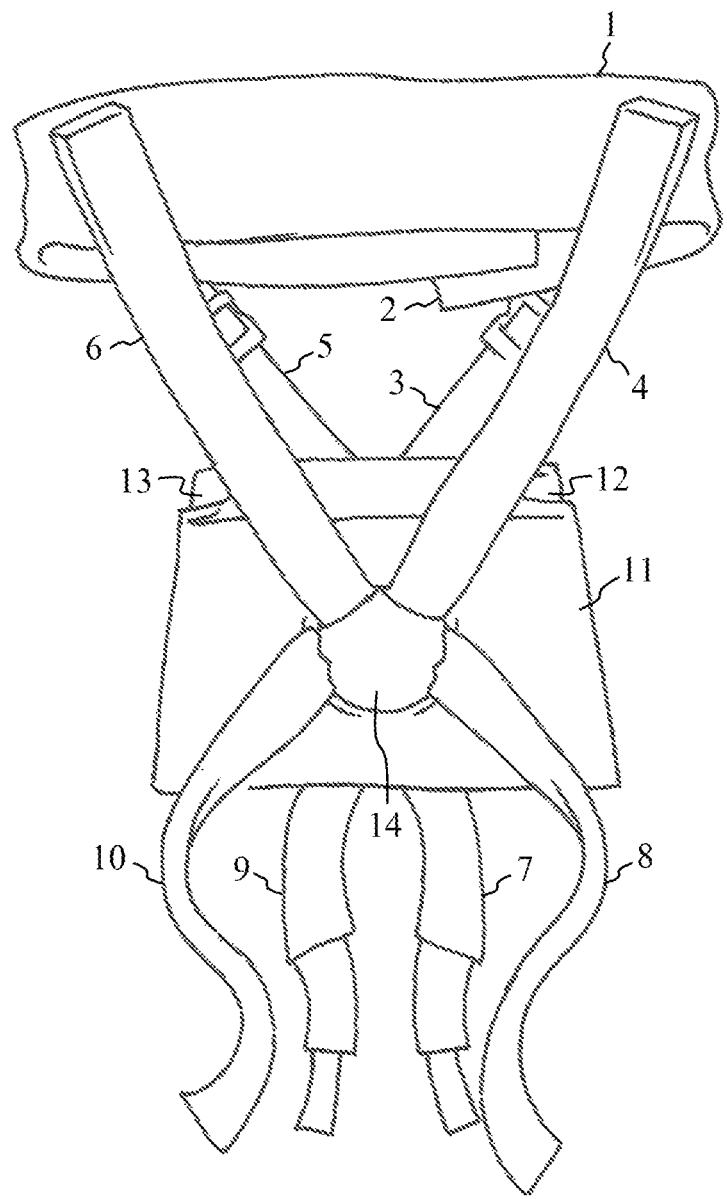
FIG. 1 shows a schematic back view of a wearable physical rehabilitation device in accordance with one exemplary embodiment.

Various embodiments of the present disclosure are further described in more detail with reference to the accompanying drawings. However, the present disclosure may be embodied in many other forms and should not be construed as limited to any certain structure or function discussed in the following description. In contrast, these embodiments are provided to make the description of the present disclosure detailed and complete.

According to the detailed description, it will be apparent to the ones skilled in the art that the scope of the present disclosure encompasses any embodiment thereof, which is disclosed herein, irrespective of whether this embodiment is implemented independently or in concert with any other embodiment of the present disclosure. For example, the device disclosed herein may be implemented in practice by using any numbers of the embodiment's provided herein. Furthermore, it should be understood that any embodiment of the present disclosure may be implemented using one or more of the features presented in the appended claims.

The word "exemplary" is used herein in the meaning of "used as an illustration". Unless otherwise stated, any embodiment described herein as "exemplary" should not be construed as preferable or having an advantage over other embodiments.

Any positioning terminology, such as "left", "right", "front", "back/rear", "top", "bottom", "above" "below", "upper", "lower", "horizontal", "vertical", etc., may be used herein for convenience to describe one element's or feature's relationship to one or more other elements or features in accordance with the figures. It should be apparent that the positioning terminology is intended to encompass different orientations of the apparatus disclosed herein, in addition to the orientation(s) depicted in the figures. As an example, if one imaginatively rotates the apparatus in the figures 90 degrees clockwise, elements or features described as "left" and "right" relative to other elements or features would then be oriented, respectively, "above" and "below" the other elements or features. Therefore, the positioning terminology used herein should not be construed as any limitation of the invention.

Although the numerative terminology, such as "first", "second", "third", "fourth", etc., may be used herein to describe various elements or features, these elements or features should not be limited by this numerative terminology. This numerative terminology is used herein only to distinguish one feature or element from another feature or element. For example, a first additional pair of ascending adjustable-length straps and a second additional pair of ascending adjustable-length straps which are discussed herein could be renamed a second additional pair of ascending adjustable-length straps and a first additional pair of ascending adjustable-length straps, respectively, without departing from the teachings of the invention.

The exemplary embodiment's disclosed herein relates to a wearable physical rehabilitation device comprising a 3D wedge-like structure made of polyurethane (PU) foam (e.g., Blue high-density PU foam or other suitable material having similar properties) and arranged between the thighs of a subject or patient, as well as straps by which the 3D wedge-like structure is attached to a supporting or fastening belt above the posterior and anterior locations of the Iliac crests (side hip bones) and is also fixed at midpoint of both femurs to hold the 3D wedge-like structure in place. This resulting pelvic posture will shorten the abductor muscles and external rotator muscles of the hip joint, thereby placing them at a mechanical advantage to function more efficiently and have a better strength and balance. As the subject begins to ambulate with the device on, the muscles will then be able to support the hips, knees, and ankles better and provide more improved efficiencies and less taxing functional movements (in both the upper and lower extremities). In conjunction with the 3D wedge-like structure, there is an integral control handle-provided support apparatus that utilizes a saddle-shaped structure for receiving buttocks of the subject. The saddle-shaped structure may be used to control and support both the pelvis and trunk anteriorly via the handle to direct sufficient forces by a physical therapist or a healthcare provider. The device may also comprise additional straps ascending upward around the back of the neck and linked together via Velcro or other suitable attachment means for the purpose of maintaining the control handle at an easily accessible position for the physical therapist or healthcare provider. The control handle is supported by a strap supported, for example, but not limited to an apron around the back of neck which may also be in a form of another suitable support configuration, such as a shoulder harness. The neck straps descend from around the neck to the control handle that may be located at the xiphoid/umbilical region. In addition, support patches located on both sides of the upper edge of the saddle-shaped structure may be used to provide proper posterior attachment of the saddle-shaped structure to the 3D wedge-like structure.

Figure 4:
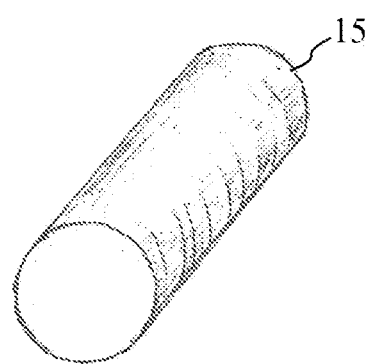
FIG. 4 shows a schematic isometric view of a variable density pliable filler which can be inserted into a tubular through hole formed in the 3D wedge-like structure of FIGS. 3A and 3B.

FIG. 1 shows a schematic back view of a wearable physical rehabilitation device in accordance with one exemplary embodiment. As shown in FIG. 1, the device comprises a supporting belt 1 which may be fitted around the waist of a subject (e.g., at the "iliums" bilaterally). In addition, the belt may be bound at the "pen" umbilical region by a Velcro or other suitable similar attachment means 2. The device also comprises a 3D wedge-like structure 11 (e.g., in the form of a 3D isosceles trapezoidal wedge with substantially parallel cephal and caudal surfaces) that may be made, for example, of Blue high-density PU foam or other suitable material having similar properties. The 3D wedge-like structure 11 is supported by ascending adjustable-length straps 4, 6 posteriorly (relative to the body of the subject) and by ascending adjustable-length straps 3, 5 anteriorly (relative to the body of the subject). Each of the straps 4, 6 and 3, 5 may be made of nylon fabric or other suitable material having similar properties. The straps 4, 6 and 3, 5 are anchored via Velcro, buckle or other suitable attachment means to the superior supporting belt 1. When attached to each other (e.g., via Velcro or buckle attachment means), the strap 3, 4 is a single continuous ascending strap passing through a hollow tubular hole 14 in the 3D wedge-like structure 11, where it is bounded to the 3D wedge-like structure 11 internally as it passes through the hole 14. The same is true for the straps 5, 6 which, when attached to each other, also form a single continuous ascending strap. The hole 14 may be approximately 3" in diameter and formed in the center of the 3D wedge-like structure 11, and each of the continuous ascending straps (i.e., those formed by the straps 3, 4 and the straps 5, 6) passes through the hole 14. The hole 14 may be adjusted for stiffness by inserting a cylindrical variable-density pliable material 15 (see FIG. 4). Since all patients are of different body structure, some of them may require more resistant spacing at the groin and upper leg area according to their body mass, so that a wider base of stance is maintained at their footing. The pliable material 15 is usually shaped as cylinder 3"×6" filled with various density of material. The device also comprises lateral adjustable-length straps 7, 8 that are configured to attach to and around the right thigh of the subject, and lateral adjustable-length straps 9, 10 that are configured to attach to and around the left thigh of the subject. Again, each of the pair of the straps 7, 8 and the pair of the straps 9, 10 forms a single continuous lateral strap when they are attached to each other around the corresponding thigh of the subject.

Figure 2:
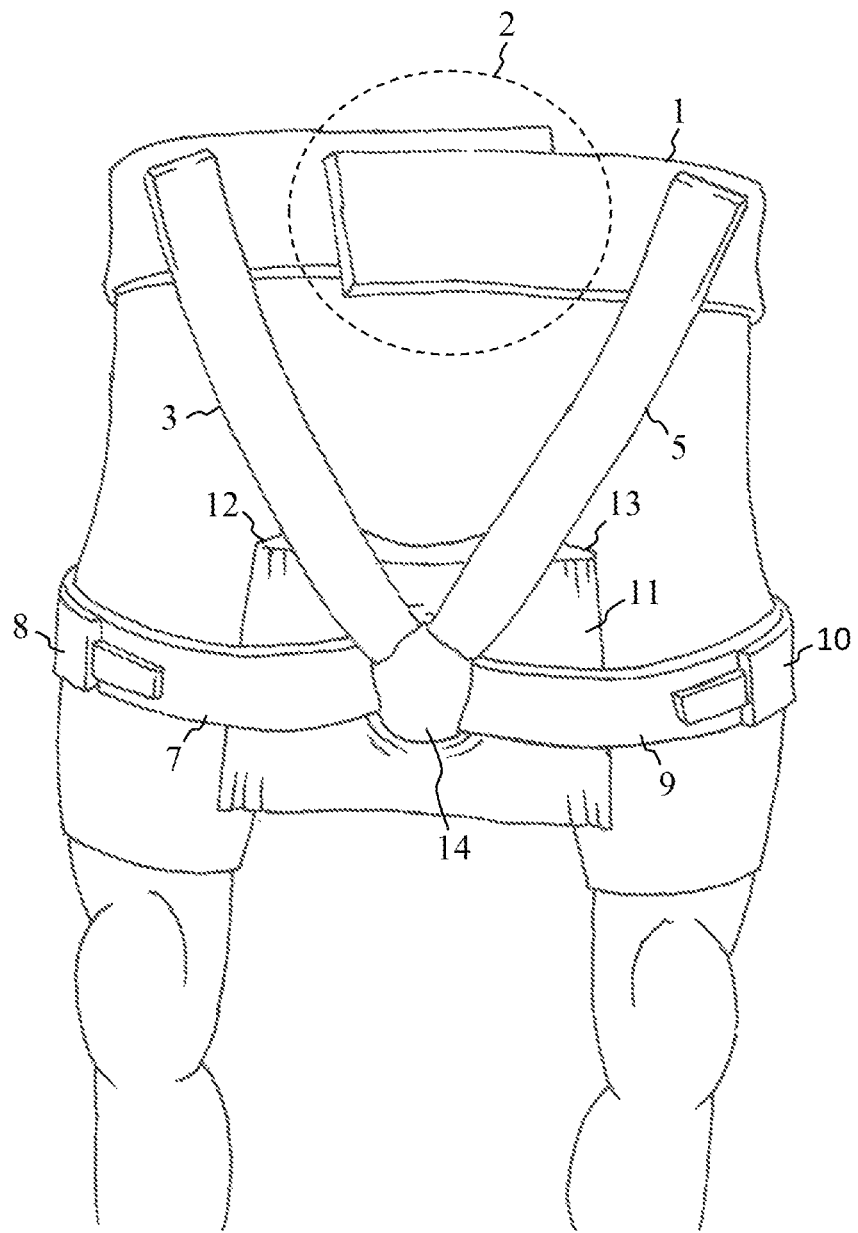
FIG. 2 shows a schematic front view of the physical rehabilitation device, when worn by a subject, in accordance with one exemplary embodiment.

FIG. 2 shows a schematic front view of the same physical rehabilitation device, when worn by the subject, in accordance with one exemplary embodiment. As follows from FIGS. 1 and 2, each of the pair of the straps 3, 4 and the pair of the straps 5, 6 forms a single continuous ascending strap that loops through the hole 14 of the 3D wedge-like structure 11 and out the opposing side where their ends terminate at the anchoring points on the belt 1 which suspends the 3D wedge-like structure 11 through Velcro attachments or other suitable attachment means and maintains the original position of the 3D wedge-like structure 11 through ambulation and functional body tasks, for example, bending, reaching, squatting, and overall general body movements. The straps 3, 4 and 5, 6 may also ascend/descend bilaterally, as well as anteriorly/posteriorly down to the level of the inguinal at the hole, 14, to loop through it in the 3D wedge-like structure 11 (for interior attachment within the hole 14, using any suitable mechanical bonding or chemical bonding adhering means (not shown)).

As noted above, the straps 7, 8 and 9, 10 may be made of Velcro-friendly material at their ends to provide for various size thighs to extend horizontally/laterally to attach to and around the mid thighs bilaterally (one length of strap per side). Moreover, the straps 7, 8 and 9, 10 pass anteriorly and posteriorly through the hole 14 and may be anchored to the inner walls of the hole 14 via mechanical fixation or chemical adhesion (not shown).

Figure 3A:
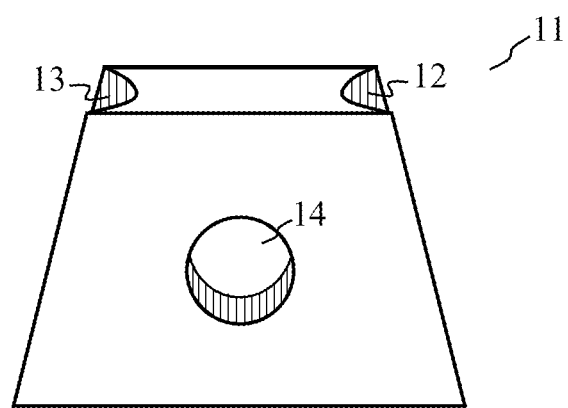
FIGS. 3A and 3B shows different schematic views of a 3D wedge-like structure included in the physical rehabilitation device of FIGS. 1 and 2, namely.
Figure 3B:
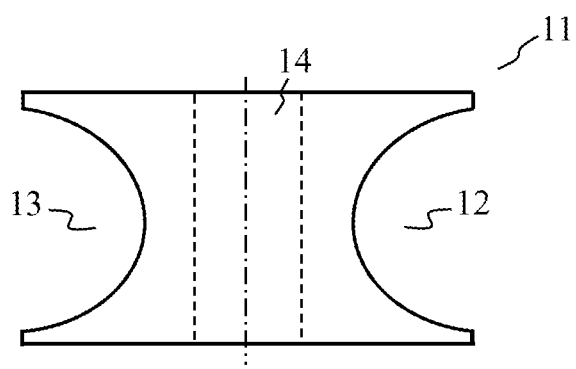

As can be seen in FIGS. 1 and 2, the 3D wedge-like structure may have two recesses 12, 13 on its lateral sides, which are shaped to fit the inner thighs of the subject. The recesses 12, 13 may be also seen in different schematic views of the 3D wedge-like structure 11 in FIGS. 3A and 3B. With these recesses 12, 13, it is convenient for the subject to hold the 3D wedge-like structure between the thighs while in standing, sitting, lying positions and/or during functional bodily movements. The interior of the hole 14 may have a suitable anchoring or attachment means available via mechanical fixation or chemical adhesion (not shown) for looping through of the ascending/descending stabilizing straps, as well as horizontal stabilizing straps.

Figure 5:
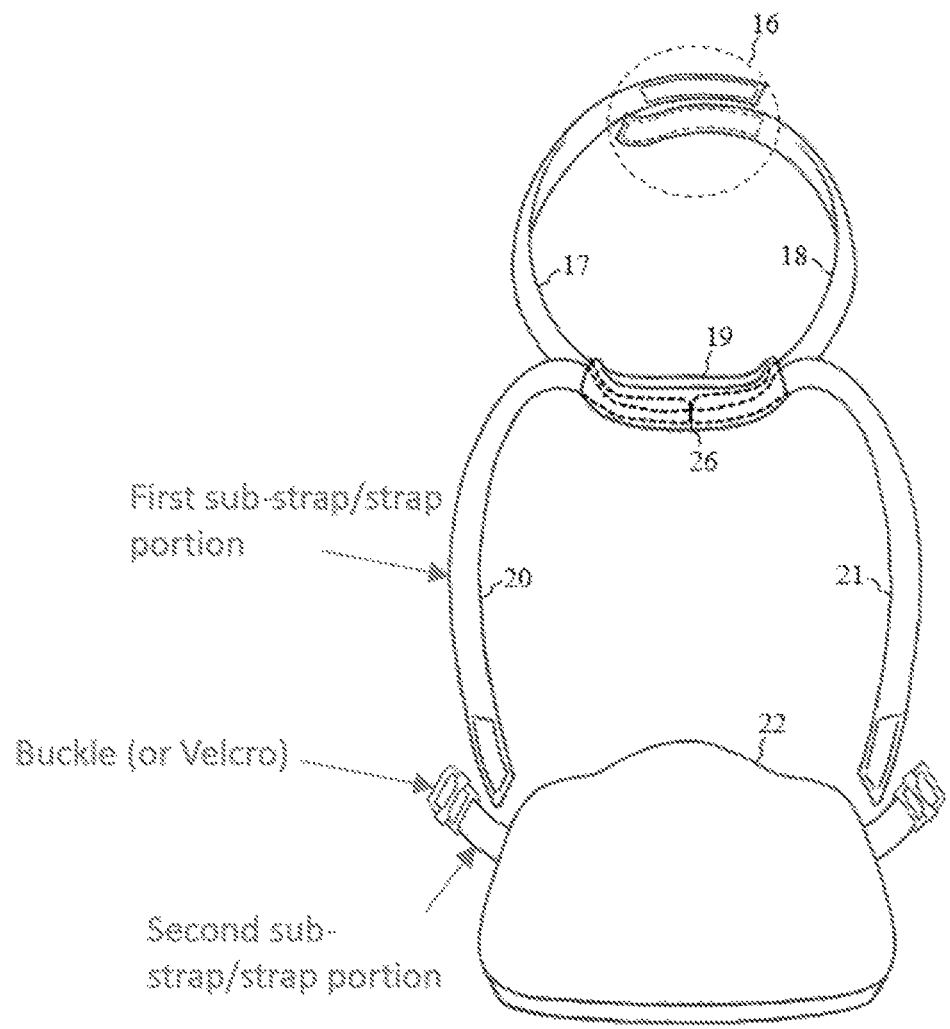
FIG. 5 shows a schematic view of a saddle-shaped structure with a control handle in accordance with one exemplary embodiment; the saddle could be Velcro, Buckle or any suitable connection means; the permanent connections at the saddle can be decided with further engineering research on stresses and strengths at that connection location, due to possible connection failures leading to injury of subject/patient.
Figure 6:
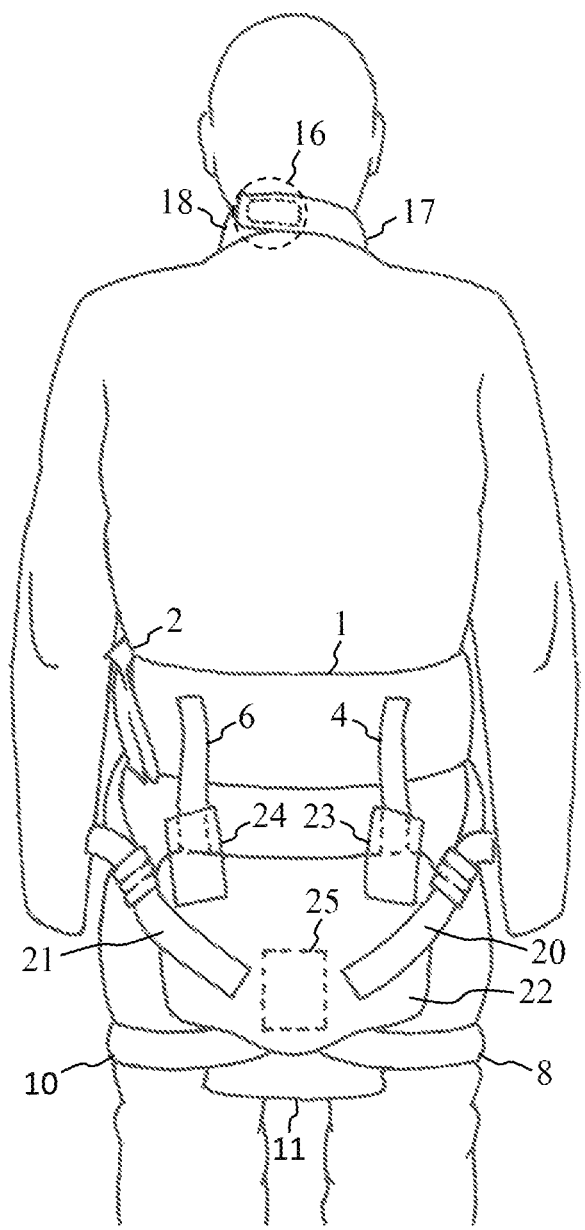
FIG. 6 schematically shows how the saddle-shaped structure of FIG. 5 may be attached to the physical rehabilitation device of FIGS. 1 and 2.

FIG. 5 shows a schematic view of a saddle-shaped structure 22 with a control handle 19 in accordance with one exemplary embodiment. FIG. 6 schematically shows how the saddle-shaped structure 22 may be attached to the physical rehabilitation device. The saddle-shaped structure 22 is used to control the pelvis and trunk of the subject using forces directed anteriorly and superiorly from the front of the body of the subject through the handle 19 connected to the saddle-shaped structure 22 posteriorly, via Velcro friendly additional descending straps 20, 21 (or straps using any other suitable attachment means, such as buckles, may be used). The saddle-shaped structure 22 may be also Velcro-friendly. The saddle-shaped structure 22 is initially held in place during installation of the 3D wedge-like structure 11 on the subject, via the attachment of three support patches 23, 24, 25. Two support patches 23 and 24 are located bilaterally on upper lateral edges of the saddle-shaped structure 22. The two support patches 23, 24 both extend off the top edge of the saddle-shaped structure 22, the extending ends attach to the left and right straps 4, 6 approximately mid-way between the saddle-shaped structure 22 and the superior supporting belt 1. The support patch 25 is located at the middle area of the saddle-shaped structure 22, between the saddle-shaped structure 22 and the straps 4, 6 just before they turn to pass through the hole 14. The support patch 25 may be adhered to both the straps 4, 6 and the saddle-shaped structure 22 via elected Velcro patch properties.

As also follows from FIGS. 5 and 6, there is a set of additional ascending straps 17, 18 from each side of the control handle 19 to terminate behind the neck of the subject at an (e.g., Velcro) attachment point 16. This is to conveniently support the location of the control handle 19 to be easily accessed by a healthcare provider. The control handle 19 is comprised of a suitable rigid hollow hand grippable structure that allows the straps 17, 20 (which form one complete strap when they are attached to each other) and the strap 18, 21 (which also form one complete strap when they are attached to each other) to enter through the corresponding side of the control handle 19 equally and to be bound to each other in the interior of the control handle 19 (see an attachment point 26 in FIG. 5). For example, the straps may be lapped over each other and sewn together or chemically, mechanically adhered to each other inside the control handle 19. This lacing through the control handle 19 more freely eliminates one-sided force production by allowing it to slide freely as needed for the subject's stability and avoid twisting or torquing of the subject's body during use of the physical rehabilitation device.

Lastly, the physical rehabilitation device disclosed herein may be acclimated into a pair of slip-on wearable garments, such as shorts, using spandex or suitable material for the lower extremities. Furthermore, the physical rehabilitation device disclosed herein may be taken off through Velcro or other suitable attachment means at the waistline, if chosen to do so by a care provider or the subject himself/herself. In addition, a moisture resistant covering may be placed over the 3D wedge-like structure 11 to reduce body fluids contaminating the 3D wedge-like structure 11. The 3D wedge-like structure 11 and the attached straps are washable.

Although the exemplary embodiments of the present disclosure are described herein, it should be noted that any various changes and modifications could be made in the embodiments of the present disclosure, without departing from the scope of legal protection which is defined by the appended claims. In the appended claims, the word "comprising" does not exclude other elements or operations, and the indefinite article "a" or "an" does not exclude a plurality. The mere fact that certain measures are recited in mutually different dependent claims does not indicate that a combination of these measures cannot be used to advantage.

The invention claimed is:

1. A wearable physical rehabilitation device comprising:
a supporting belt configured to be fitted around a waist of a subject;
a 3D wedge structure made of polyurethane foam and configured to be arranged between thighs of the subject, the 3D wedge structure having a tubular through hole;
a saddle structure configured to receive buttocks of the subject, the saddle structure being arranged posteriorly relative to the 3D wedge structure;
a hollow control handle configured to be arranged anteriorly relative to the body of the subject;
a pair of ascending adjustable-length straps each passing through the tubular through hole and configured to directly attach the 3D wedge structure to the supporting belt anteriorly and posteriorly relative to the body of the subject;
a pair of lateral adjustable-length straps each passing through the tubular through hole and configured to attach the 3D wedge structure to and around a respective one of the thighs of the subject;
a pair of descending adjustable-length straps each extending from the hollow control handle and configured to directly attach the hollow control handle to the saddle structure; and
an additional pair of ascending adjustable-length straps extending from the hollow control handle and configured to attach to each other behind a neck of the subject.

2. The device of claim 1, wherein each strap in at least one of the pair of ascending adjustable-length straps, the pair of lateral adjustable-length straps and the pair of descending adjustable-length straps has two strap portions attached to each other by using attachment means.

3. The device of claim 2, wherein the attachment means are a hook and loop fastener or buckle.

4. The device of claim 1, wherein the 3D wedge structure further comprises two lateral recesses each shaped to be configured to fit an inner surface of a respective one of the thighs of the subject.

5. The device of claim 1, wherein the 3D wedge structure is a 3D isosceles trapezoidal wedge.

6. The device of claim 1, wherein the 3D wedge structure further comprises a variable density pliable filler shaped to be inserted into the tubular through hole.

7. The device of claim 1, wherein each strap in at least one of the pair of ascending adjustable-length straps, the pair of lateral adjustable-length straps, the pair of descending adjustable-length straps and the additional pair of ascending adjustable-length straps is made of nylon fabric.

8. The device of claim 1, wherein each strap of the pair of ascending adjustable-length straps has ends attached to the supporting belt anteriorly and posteriorly by using a hook and loop attachment means.

9. The device of claim 1, wherein each strap of the pair of descending adjustable-length straps has an end attached to each side of the saddle structure by using a hook and loop attachment means.

10. The device of claim 1, wherein the straps of the additional pair of ascending adjustable-length straps are configured to attach to each other behind the neck of the subject by using a hook and loop attachment means.

* * * * *